(12) United States Patent
De Sapio et al.

(10) Patent No.: US 9,610,036 B1
(45) Date of Patent: Apr. 4, 2017

(54) QUANTIFYING MUSCLE AND TENDON FATIGUE DURING PHYSICAL EXERTION

(71) Applicant: The Boeing Company, Chicago, IL (US)

(72) Inventors: Vincent De Sapio, Westlake Village, CA (US); Michael Dickson Howard, Westlake Village, CA (US); Rush Frederick Green, Seattle, WA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 15/061,250

(22) Filed: Mar. 4, 2016

(51) Int. Cl.
*G08B 23/00* (2006.01)
*A61B 5/22* (2006.01)
*A63B 24/00* (2006.01)
*G08B 21/02* (2006.01)
*G06F 17/50* (2006.01)

(52) U.S. Cl.
CPC ............ *A61B 5/22* (2013.01); *A63B 24/0003* (2013.01); *A63B 24/0062* (2013.01); *G06F 17/5009* (2013.01); *G08B 21/02* (2013.01)

(58) Field of Classification Search
CPC ... A61B 5/22; A63B 24/0003; A63B 24/0062; G06F 17/5009; G08B 21/02
USPC ...... 340/573.1; 600/301, 393, 546, 547, 587
See application file for complete search history.

(56) References Cited

U.S. PATENT DOCUMENTS

2005/0283204 A1* 12/2005 Buhlmann ........... A61B 5/1107
607/48
2008/0319515 A1* 12/2008 Priori ....................... A61N 1/20
607/75
2015/0141872 A1* 5/2015 Andrisani .............. A61B 5/225
600/587
2015/0170530 A1* 6/2015 Damman .......... G06F 17/30864
700/91
2015/0182160 A1* 7/2015 Kim ..................... A61B 5/0488
600/301

(Continued)

OTHER PUBLICATIONS

Ma et al., "A new muscle fatigue and recovery model and its ergonomics application in human simulation," International Conference on Integrated Design and Manufacturing in Mechanical Engineering (IDMME)—Virtual concept, Oct. 2008, 10 pages.
Liu et al., "A Dynamical Model of Muscle Activation, Fatigue, and Recovery," Biophysical Journal, vol. 82, Issue 5, May 2002, 16 pages.

(Continued)

*Primary Examiner* — Ojiako Nwugo
(74) *Attorney, Agent, or Firm* — Yee & Associates, P.C.

(57) ABSTRACT

A method and apparatus for monitoring musculoskeletal performance. A person repeatedly performing a physical task is monitored using a sensor system to generate task performance data. A simulation of the person performing the physical task over a number of cycles is run using a musculoskeletal model for the person and at least one of the task performance data and task description data. Muscle activation data and tendon force data are generated based on the simulation. Muscle fatigue and tendon fatigue resulting from performing the physical task are simulated for each cycle using a fatigue model system, the muscle activation data, and the tendon force data. The musculoskeletal model is adjusted to account for the muscle fatigue and the tendon fatigue after each cycle and prior to a next cycle. A prediction is made as to when a predetermined risk threshold for the person is reached based on the simulation.

21 Claims, 10 Drawing Sheets

(56) References Cited

U.S. PATENT DOCUMENTS

2016/0157749 A1* 6/2016 Bohorquez .......... A61B 5/0537
600/393

OTHER PUBLICATIONS

De Sapio, "An approach for goal-oriented neuromuscular control of digital humans in physics-based simulations," International Journal of Human Factors Modelling and Simulation, vol. 4, No. 2, copyright 2004, 24 pages.
Fung et al., "Early response to tendon fatigue damage accumulation in a novel in vivo model," Journal of Biomechanics, vol. 43, No. 2, Jan. 2010, 15 pages.
Smith et al., "A conceptual framework for computational models of Achilles tendon homeostasis," Wiley Interdisciplinary Review Systems Biology and Medicine, vol. 5, Issue 5, Sep. 2013, 16 pages.
Thelen et al., "Using computed muscle control to generate forward dynamic simulations of human walking from experimental data," Journal of Biomechanics, vol. 39, copyright 2006, 9 pages.
Thelen et al., "Generating dynamic simulations of movement using computed muscle control," Journal of Biomechanics, vol. 36, copyright 2003, 8 pages.
Wren et al., "Effects of Creep and Cyclic Loading on the Mechanical Properties and Failure of Human Achilles Tendons," Annals of Biomedical Engineering, vol. 31, No. 6, copyright 2003, 8 pages.
Zajac, "Muscle and Tendon: Properties, Models, Scaling, and Application to Biomechanics and Motor Control," Critical Review in Biomedical Engineering, vol. 17, Issue 4, copyright 1989, 52 pages.

* cited by examiner

QUANTIFYING MUSCLE AND TENDON FATIGUE DURING PHYSICAL EXERTION

BACKGROUND INFORMATION

1. Field

The present disclosure relates generally to musculoskeletal performance. More particularly, the present disclosure relates to a method and apparatus for monitoring and quantifying musculoskeletal performance for the repeated performance of a physical task for a manufacturing operation.

2. Background

Manufacturing operations often require laborers to perform different types of repetitive physical tasks. For example, without limitation, painting an aircraft structure using a handheld painting tool may require that a laborer perform a series of painting strokes. As another example, a laborer may manually sand a structure by moving a sanding tool in a circular direction a repeated number of times.

Performing a physical task a repeated number of times may sometimes result in undesired muscle exhaustion and undesired tendon compromise. For example, performing a particular physical task repeatedly may involve the use of a particular key set of muscles. Over time, performing this physical task repeatedly may result in muscle fatigue and tendon fatigue. Muscle fatigue reduces the strength of a muscle. Tendon fatigue reduces the structural capacity of a tendon.

Performing a physical task when the strength of one or more certain muscles has been reduced beyond a selected threshold or when the structural capacity of one or more certain tendons has been reduced beyond a selected threshold may increase the potential for musculoskeletal injury. A musculoskeletal injury may include a muscle injury, a joint injury, a tendon breakdown, or a combination thereof. Consequently, performing repetitive physical tasks during certain manufacturing operations may cause undesired risk to the laborers performing these physical tasks. Therefore, it would be desirable to have a method and apparatus that take into account at least some of the issues discussed above, as well as other possible issues.

SUMMARY

In one illustrative embodiment, a method is provided for monitoring musculoskeletal performance. A performance of a person repeatedly performing a physical task is monitored using a sensor system to generate task performance data. A simulation of the person performing the physical task over a number of cycles is run by a computer system using a musculoskeletal model for the person and at least one of the task performance data and task description data. Muscle activation data and tendon force data are generated by the computer system based on the simulation for each cycle in the number of cycles. Muscle fatigue and tendon fatigue that results from performing the physical task are simulated by the computer system for each cycle in the number of cycles using a fatigue model system, the muscle activation data, and the tendon force data. The musculoskeletal model is adjusted by the computer system to account for the muscle fatigue and the tendon fatigue after each cycle in the number of cycles and prior to a next cycle beginning. The computer system predicts when a predetermined risk threshold for the person is reached based on the simulation.

In another illustrative embodiment, an apparatus comprises a sensor system, a musculoskeletal simulator module in communication with the sensor system, a fatigue modeler module, and a control module. The sensor system monitors a person repeatedly performing a physical task to generate task performance data. The musculoskeletal simulator module in communication with the sensor system is implemented in a computer system. The musculoskeletal simulator module in communication with the sensor system runs a simulation of the person performing the physical task over a number of cycles using a musculoskeletal model for the person and at least one of the task performance data or task description data. The musculoskeletal simulator module in communication with the sensor system generates muscle activation data and tendon force data based on the simulation for each cycle in the number of cycles. The fatigue modeler module is implemented in the computer system that simulates muscle fatigue and tendon fatigue that results from performing the physical task for each cycle in the number of cycles using a fatigue model system, the muscle activation data, and the tendon force data. The musculoskeletal model is adjusted during the simulation to account for the muscle fatigue and the tendon fatigue after each cycle in the number of cycles and prior to a next cycle beginning. The control module is implemented in the computer system and predicts when a predetermined risk threshold for the person is reached based on the.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account different considerations. For example, the illustrative embodiments recognize and take into account that it may be desirable to have a method and apparatus for analyzing the effect of repetitive musculoskeletal motion on muscle exhaustion and tendon compromise. In particular, the illustrative embodiments recognize and take into account that it may be desirable to have a method and apparatus for simulating muscle fatigue and tendon fatigue associated with the repeated performance of a physical task in a manner that allows a task performance profile for performing the physical task to be created.

The task performance profile may indicate how many repetitions or iterations of the physical task can be performed before a period of rest should be taken to avoid an undesired level of risk of injury. For example, the task performance profile may indicate that for a particular physical task, three minutes of rest should be taken after every 15 repetitions of the physical task.

The illustrative embodiments recognize and take into account that it may also be desirable to have a method and apparatus capable of monitoring and quantifying the musculoskeletal performance of a person in real-time while the person is repeatedly performing a physical task. In particular, it may be desirable to have a method and apparatus capable of warning the person before muscle exhaustion and tendon compromise lead to a risk of musculoskeletal injury that exceeds an acceptable risk threshold.

Thus, the illustrative embodiments provide a method and apparatus for monitoring and quantifying musculoskeletal performance for the repeated performance of a physical task for a manufacturing operation. In one illustrative embodiment, a method is provided for monitoring musculoskeletal performance. A simulation of a person performing a physical task over a number of cycles is run by a computer system using a musculoskeletal model for the person and task description data. Muscle activation data and tendon force data are generated by the computer system based on the simulation for each cycle in the number of cycles. Muscle fatigue and tendon fatigue that results from performing the physical task are simulated by the computer system for each cycle in the number of cycles using a fatigue model system, the muscle activation data, and the tendon force data. The musculoskeletal model is adjusted by the computer system to account for the muscle fatigue and the tendon fatigue after each cycle in the number of cycles and prior to a next cycle beginning.

Figure 1:
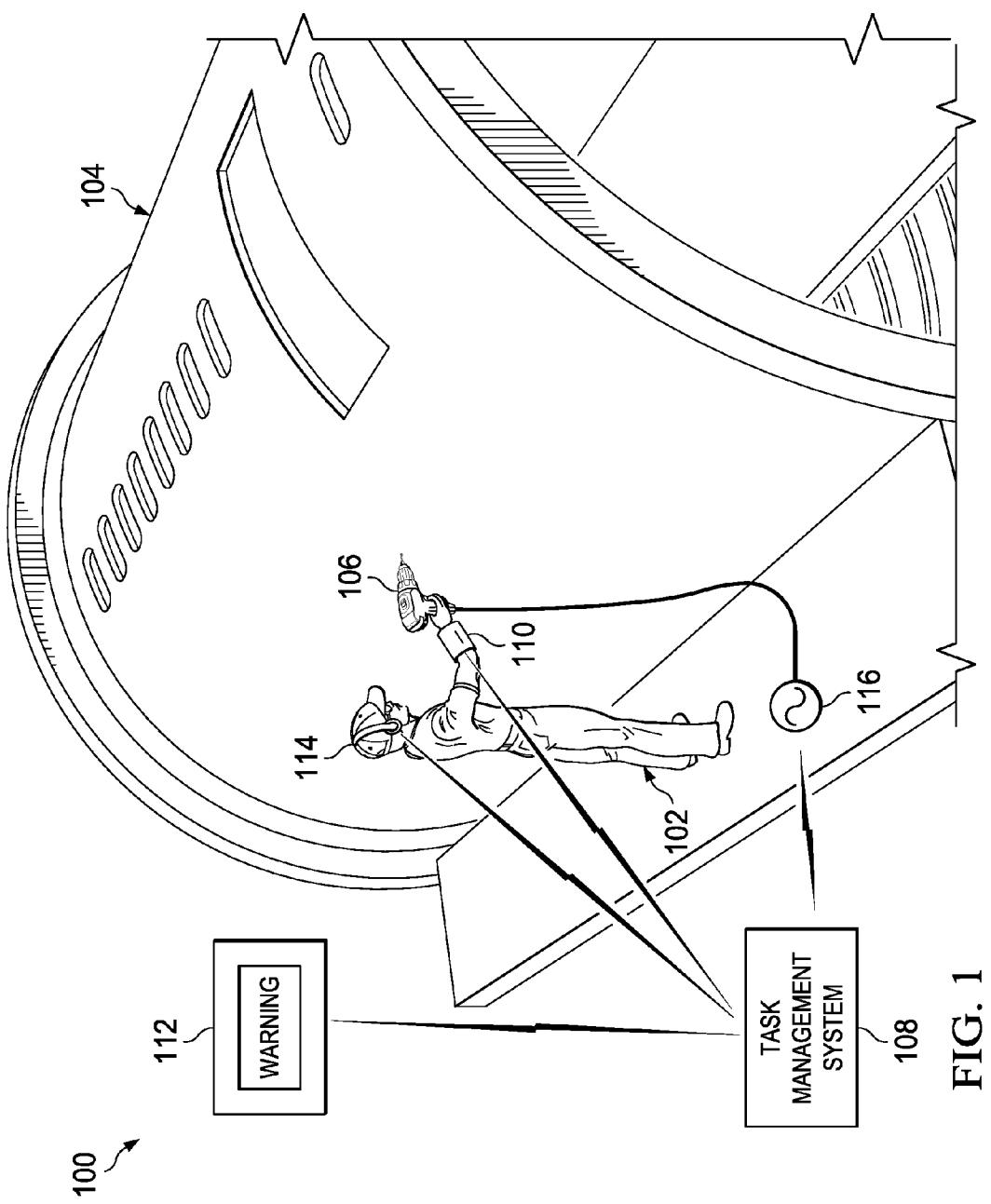
FIG. 1 is an illustration of a manufacturing environment in accordance with an illustrative embodiment.

Referring now to the figures and, in particular, with reference to FIG. 1, an illustration of a manufacturing environment is depicted in accordance with an illustrative embodiment. In FIG. 1, manufacturing environment 100 may be an environment in which operator 102 is working on aircraft structure 104. As depicted, operator 102 may use power tool 106 to perform a particular type of task repeatedly.

In one illustrative example, this task may be the drilling of a hole into aircraft structure 104. Power tool 106 may take the form of a handheld drill. For example, without limitation, operator 102 may use power tool 106 to drill hundreds of holes into aircraft structure 104. Operator 102 performing this type of drilling may result in muscle exhaustion and tendon fatigue over time.

Task management system 108 is used to monitor and quantify the musculoskeletal performance of operator 102 while operator 102 performs drilling operations. In this illustrative example, task management system 108 includes sensor system 110, display device 112, and audio device 114. Sensor system 110 is positioned over the arm of operator 102 and measures motion and force data as operator 102 performs drilling operations.

Task management system 108 may wirelessly receive the motion and force data from sensor system 110. Task management system 108 uses this data and a musculoskeletal model to predict when a risk for musculoskeletal injury is beyond an acceptable risk threshold. A musculoskeletal injury may comprise one or more muscle injuries, joint injuries, tendon breakdowns, or a combination thereof.

In one illustrative example, task management system 108 displays a visual warning indicator on display device 112 to alert operator 102 of the risk. In another illustrative example, task management system 108 sends an audible alarm to audio device 114 to audibly warn operator 102 of the risk. In still other illustrative examples, task management system 108 may send a command to power source 116 that causes power source 116 to cease providing power to power tool 106.

Figure 2:
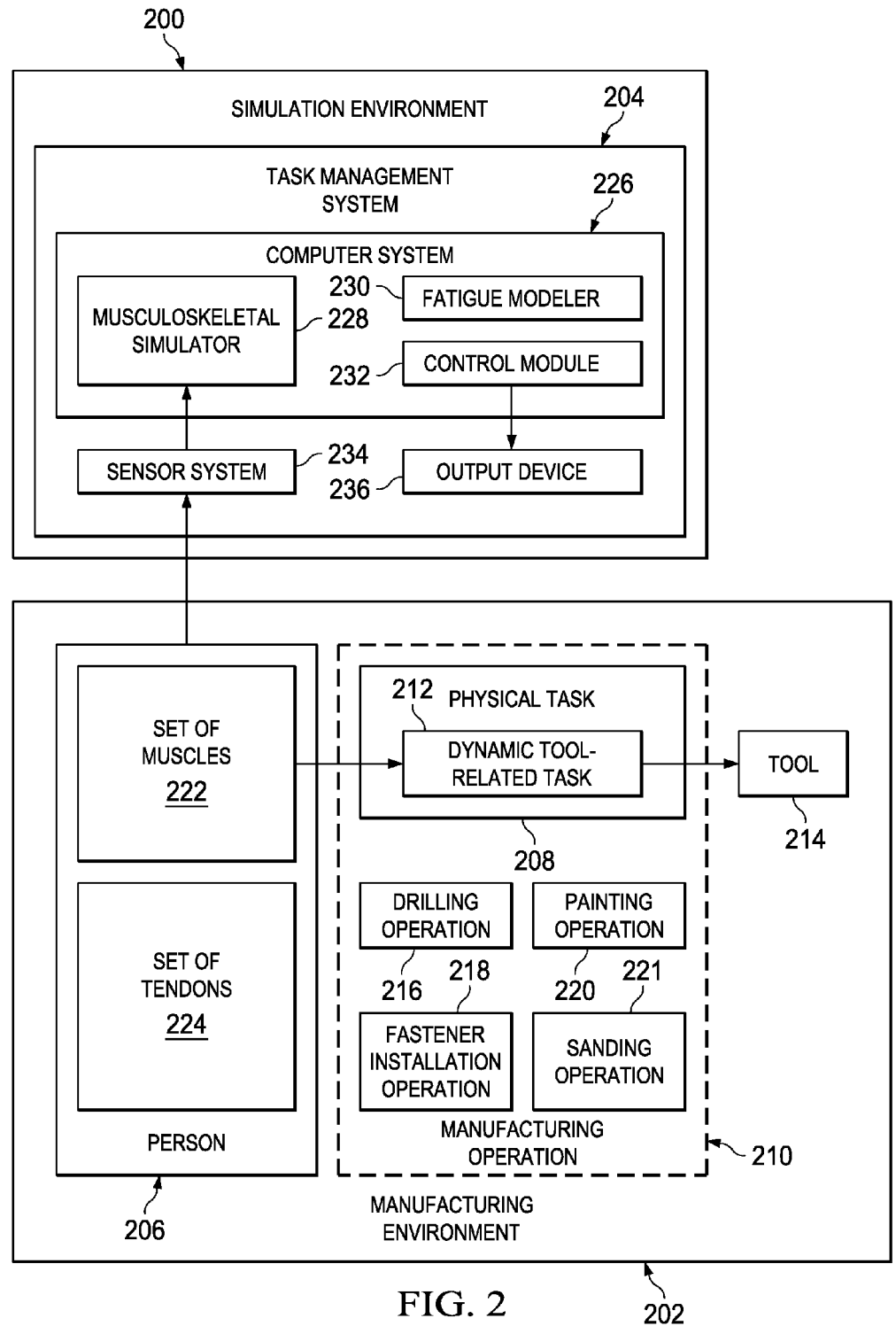
FIG. 2 is an illustration of a simulation environment and a manufacturing environment in the form of a block diagram in accordance with an illustrative embodiment.

With reference now to FIG. 2, an illustration of a simulation environment and a manufacturing environment is depicted in the form of a block diagram in accordance with an illustrative embodiment. Simulations may be run within simulation environment 200 for tasks that are performed in manufacturing environment 202.

Manufacturing environment 202 may be any environment in which manufacturing operations are to be performed. Manufacturing environment 100 in FIG. 1 is an example of one implementation for manufacturing environment 202. Depending on the implementation, manufacturing environment 202 may take the form of a manufacturing facility or factory, a shop, or some other type of location at which products are to be manufactured. Such products may include, but are not limited to, aircraft, spacecraft, ground vehicles, water vehicles, vehicle parts, electromechanical systems, and other types of systems and structures.

In this illustrative example, simulation environment 200 includes task management system 204. Task management system 204 may be used to simulate person 206 repeatedly performing physical task 208 within manufacturing environment 202. Person 206 may be, for example, without limitation, a tool operator, a factory worker, or some other type of manufacturing laborer.

Physical task 208 may be a task that is performed as part of manufacturing operation 210. In one illustrative example, physical task 208 may take the form of dynamic tool-related task 212. Dynamic tool-related task 212 may be a physical task that requires some type of motion and that is performed using tool 214. For example, person 206 may perform dynamic tool-related task 212 using tool 214 a repeated number of times as part of performing manufacturing operation 210. Depending on the implementation, manufacturing operation 210 may comprise at least one of drilling operation 216, fastener installation operation 218, painting operation 220, sanding operation 221, or some other type of operation.

As used herein, the phrase "at least one of," when used with a list of items, means different combinations of one or more of the listed items may be used and only one of the items in the list may be needed. The item may be a particular object, thing, step, operation, process, or category. In other words, "at least one of" means any combination of items or number of items may be used from the list, but not all of the items in the list may be required.

For example, without limitation, "at least one of item A, item B, or item C" or "at least one of item A, item B, and item C" may mean item A; item A and item B; item B; item A, item B, and item C; item B and item C; or item A and C. In some cases, "at least one of item A, item B, or item C" or "at least one of item A, item B, and item C" may mean, but is not limited to, two of item A, one of item B, and ten of item C; four of item B and seven of item C; or some other suitable combination.

Physical task 208 is a task that requires musculoskeletal exertion by at least one person. In other words, physical task 208 is a task that requires person 206 to use at least one muscle in a manner that places strain on at least one tendon in the body. For example, without limitation, performing physical task 208 may include lifting, squeezing, moving a hand, moving an arm, moving a leg, bending, moving a finger, stepping, carrying, some other type of physical task, or a combination thereof.

In one illustrative example, set of muscles 222 and set of tendons 224 may be critical to performing of physical task 208. For example, when a muscle in set of muscles 222 becomes overly exhausted, a tendon in set of tendons 224 becomes overly compromised, or both, the level of risk that person 206 will develop an injury may increase beyond an acceptable risk threshold. Task management system 204 may be used to provide data that can be used to instruct person 206 on how to repeatedly perform physical task 208 without the risk involved becoming too great. Further, task management system 204 may be used to monitor person 206 while person 206 repeatedly performs physical task 208 and alert person 206 when the level of risk has increased beyond the acceptable risk threshold.

Task management system 204 may be implemented using computer system 226. Computer system 226 may comprise a single computer or multiple computers in communication with each other, depending on the implementation.

As depicted, task management system 204 includes musculoskeletal simulator 228, fatigue modeler 230, control module 232, sensor system 234, and output device 236. In these illustrative examples, control module 232 may be implemented in computer system 226. Further, musculoskeletal simulator 228 is a musculoskeletal simulator module and fatigue modeler 230 is a fatigue modeler module, both of which may be implemented in computer system 226.

As used herein, a "module," such as musculoskeletal simulator 228, fatigue modeler 230, and control module 232, may be implemented using software, hardware, firmware, or a combination thereof. When software is used, the operations performed by the module may be implemented using, for example, without limitation, program code configured to run on a processor unit. When firmware is used, the operations performed by the module may be implemented using, for example, without limitation, program code and data and stored in persistent memory to run on a processor unit.

When hardware is employed, the hardware may include one or more circuits that operate to perform the operations performed by the module. Depending on the implementation, the hardware may take the form of a circuit system, an integrated circuit, an application specific integrated circuit (ASIC), a programmable logic device, or some other suitable type of hardware device configured to perform any number of operations.

A programmable logic device may be configured to perform certain operations. The device may be permanently configured to perform these operations or may be reconfigurable. A programmable logic device may take the form of, for example, without limitation, a programmable logic array, a programmable array logic, a field programmable logic array, a field programmable gate array, or some other type of programmable hardware device.

Task management system 204 is described in greater detail in FIGS. 3-4 below. In particular, musculoskeletal simulator 228, fatigue modeler 230, and control module 232 are described in greater detail in FIG. 3. Sensor system 234 and output device 236 are described in greater detail in FIG. 4 below.

Figure 3:
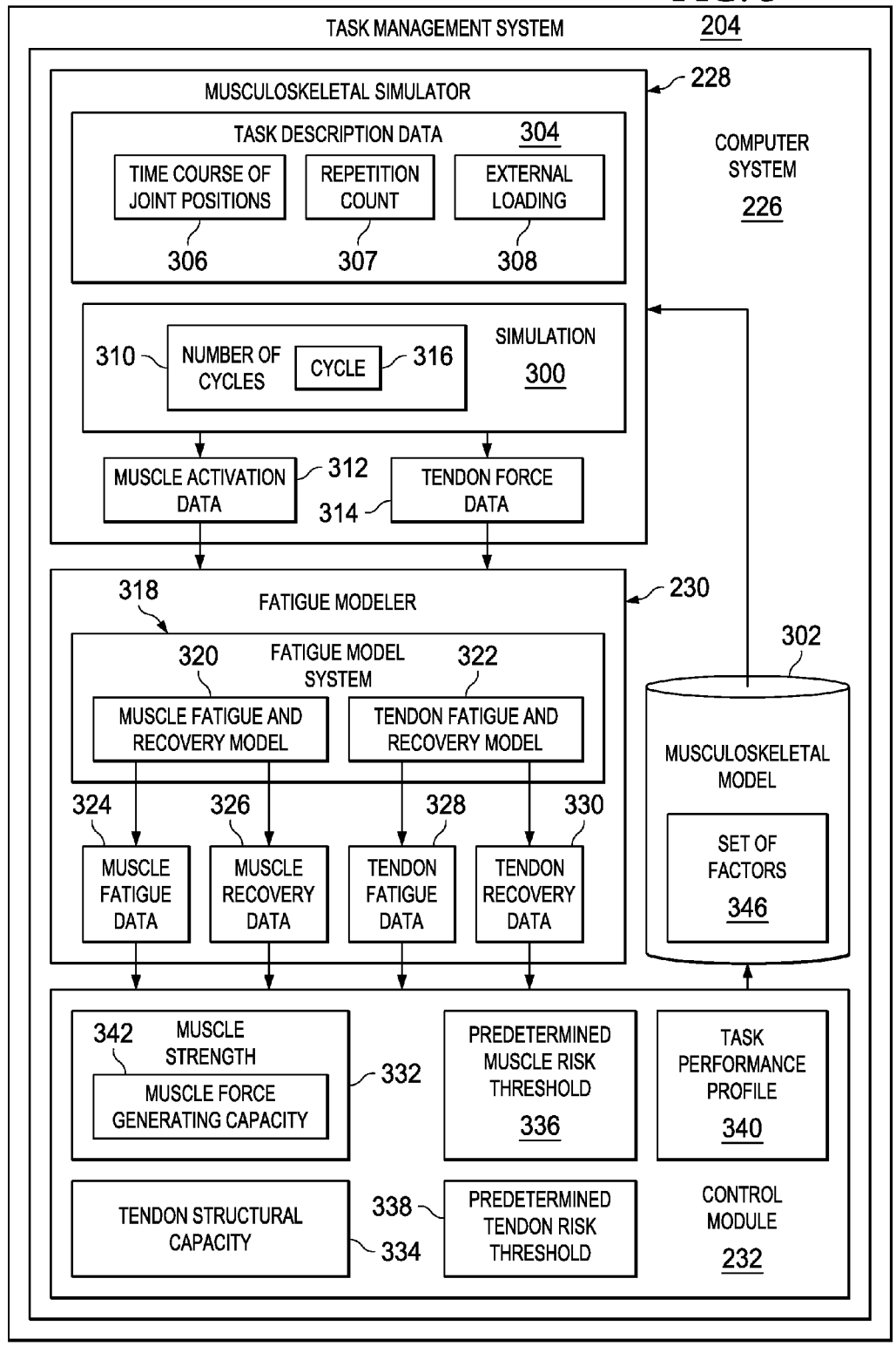
FIG. 3 is an illustration of the musculoskeletal simulator, the fatigue modeler, and the control module from FIG. 2 in the form of a block diagram in accordance with an illustrative embodiment.

With reference now to FIG. 3, an illustration of musculoskeletal simulator 228, fatigue modeler 230, and control module 232 from FIG. 2 is depicted in the form of a block diagram in accordance with an illustrative embodiment. Musculoskeletal simulator 228 may run simulation 300 of person 206 in FIG. 2 performing physical task 208 described in FIG. 2 using musculoskeletal model 302 and task description data 304.

Task description data 304 describes physical task 208 in FIG. 2. In one illustrative example, task description data 304 includes time course of joint positions 306, repetition count 307, and external loading 308. Time course of joint positions 306 may be data that identifies the various positions for joints of the musculoskeletal system during the performance of physical task 208 in FIG. 2. For example, time course of joint positions 306 may track any changes in the positions of relevant joints of the musculoskeletal system during the performance of physical task 208 in FIG. 2.

Repetition count 307 is the number of times that physical task 208 in FIG. 2 is to be performed repeatedly. External loading 308 is the loading experienced during performance of physical task 208. For example, external loading 308 may include the load imposed by at least one of tool 214 in FIG. 2, an object or structure that is being lifted as part of physical task 208, or some other type of load.

Musculoskeletal simulator 228 runs simulation 300 for number of cycles 310. When simulation 300 is run using task description data 304, number of cycles 310 may be equal in number to repetition count 307.

For each cycle in number of cycles 310, musculoskeletal simulator 228 generates muscle activation data 312 and tendon force data 314 based on simulation 300. For example, without limitation, musculoskeletal simulator 228 may generate muscle activation data 312 and tendon force data 314 for cycle 316.

In one illustrative example, to compute muscle activation data 312 for cycle 316, musculoskeletal simulator 228 may compute a muscle activation metric for set of muscles 222 in FIG. 2 needed to perform physical task 208 using musculoskeletal model 302 and task description data 304. Depending on the implementation, the muscle activation metric may be a maximum muscle activation for each muscle in set of muscles 222 in FIG. 2 as represented by musculoskeletal model 302 over cycle 316, an average muscle activation for each muscle in set of muscles 222 over cycle 316, or some other type of metric.

In one illustrative example, to compute tendon force data 314 for cycle 316, musculoskeletal simulator 228 computes a number of forces exerted on set of tendons 224 in FIG. 2 as represented by musculoskeletal model 302 that are strained when physical task 208 is performed. These forces are computed using musculoskeletal model 302 and task description data 304.

Musculoskeletal simulator 228 sends muscle activation data 312 and tendon force data 314 to fatigue modeler 230 for processing. Fatigue modeler 230 uses fatigue model system 318 to simulate muscle fatigue and tendon fatigue that results from repeatedly performing physical task 208. In particular, fatigue modeler 230 simulates the muscle fatigue and tendon fatigue for each cycle in number of cycles 310 using fatigue model system 318.

In this illustrative example, fatigue model system 318 may comprise any number of algorithms, equations, formulas, or combination thereof for modeling muscle fatigue and recovery, tendon fatigue and recovery, or both. For example, fatigue model system 318 may include muscle fatigue and recovery model 320 and tendon fatigue and recovery model 322.

Muscle fatigue and recovery model 320 may be used to generate muscle fatigue data 324 and muscle recovery data 326. Tendon fatigue and recovery model 322 is used to generate tendon fatigue data 328 and tendon recovery data 330. Muscle fatigue and recovery model 320 may include, for example, without limitation, a set of equations for estimating muscle fatigue and a set of equations for estimating muscle recovery. Similarly, tendon fatigue and recovery model 322 may include, for example, without limitation, a set of equations for estimating tendon fatigue and a set of equations for estimating tendon recovery.

Fatigue modeler 230 may send muscle fatigue data 324, muscle recovery data 326, tendon fatigue data 328, and tendon recovery data 330 to control module 232 for processing. In particular, control module 232 uses muscle fatigue data 324, muscle recovery data 326, tendon fatigue data 328, and tendon recovery data 330 to adjust musculoskeletal model 302 to account for muscle fatigue and tendon fatigue after each cycle in number of cycles 310 and prior to a next cycle beginning. In this manner, an adjusted musculoskeletal model 302 is used for each next cycle in number of cycles 310.

For example, without limitation, control module 232 uses muscle fatigue data 324, muscle recovery data 326, tendon fatigue data 328, and tendon recovery data 330 to predict muscle strength 332 for set of muscles 222 in FIG. 2 and tendon structural capacity 334 for set of tendons 224 in FIG. 2. In one illustrative example, muscle strength 332 may be measured based on muscle force generating capacity 342. Tendon structural capacity 334 may be measured based on how many more cycles a given tendon can take for a particular force before becoming comprised beyond an acceptable risk threshold.

Control module 232 adjusts musculoskeletal model 302 based on muscle strength 332 and tendon structural capacity 334 prior to musculoskeletal simulator 228 running the next cycle. In this manner, each new cycle is run using an adjusted musculoskeletal model that takes into account muscle and tendon fatigue resulting from the previous cycle.

Further, control module 232 may predict when a predetermined risk threshold has been passed based on muscle strength 332 and tendon structural capacity 334. This predetermined risk threshold may be passed when at least one of predetermined muscle risk threshold 336 or predetermined tendon risk threshold 338 has been passed. For example, without limitation, predetermined muscle risk threshold 336 may be muscle force generating capacity 342 for any muscle in set of muscles 222 in FIG. 2 that is between about 40 percent and about 80 percent. In one illustrative example, predetermined muscle risk threshold 336 is about 60 percent of a normal or full muscle force generating capacity. As another illustrative example, predetermined tendon risk threshold 338 may be tendon structural capacity 344 for any tendon in set of tendons 224 in FIG. 2 that is between about 40 percent and about 80 percent. In one illustrative example, predetermined tendon risk threshold 338 is about 60 percent of a normal or full tendon structural capacity.

Control module 232 uses the results of running simulation 300 over number of cycles 310 to generate task performance profile 340. Person 206 repeatedly performing physical task 208 in FIG. 2 according to task performance profile 340 may reduce muscle exhaustion and tendon compromise during the performance of physical task 208. For example, without limitation, task performance profile 340 may identify a pattern of intervals for performing repetitions of physical task 208 and intervals of rest that reduce muscle exhaustion and tendon compromise, to thereby reduce the risk of musculoskeletal injury.

Once task performance profile 340 has been generated, the entire process described above may be repeated using task performance profile. For example, musculoskeletal simulator 228 may run a new simulation using musculoskeletal model 302, task description data 304, and task performance profile 340. The cycles run for this new simulation may be tailored based on task performance profile 340. In some cases, the new results of the simulation may be used to further refine task performance profile 340.

In this manner, task management system 204 may run any number of simulations to generate task performance profile 340. Person 206 may then perform physical task 208 according to task performance profile 340 to reduce muscle exhaustion and tendon compromise and thereby reduce the risk of undesired musculoskeletal injury.

In some illustrative examples, task performance profile 340 may be tailored to set of factors 346 for person 206. For example, without limitation, musculoskeletal model 302 may be tuned to a particular demographic makeup based on set of factors 346. Set of factors 346 includes at least one of age, height, weight, body shape, gender, ectomorph characteristics, mesomorph characteristics, endomorph characteristics, or some other type of factor. By using a tuned musculoskeletal model 302 to run simulations, task performance profile 340 that is generated based on these simulations may also be specifically tuned for a particular anthropometric makeup of a person, demographic factors, or both.

Figure 4:
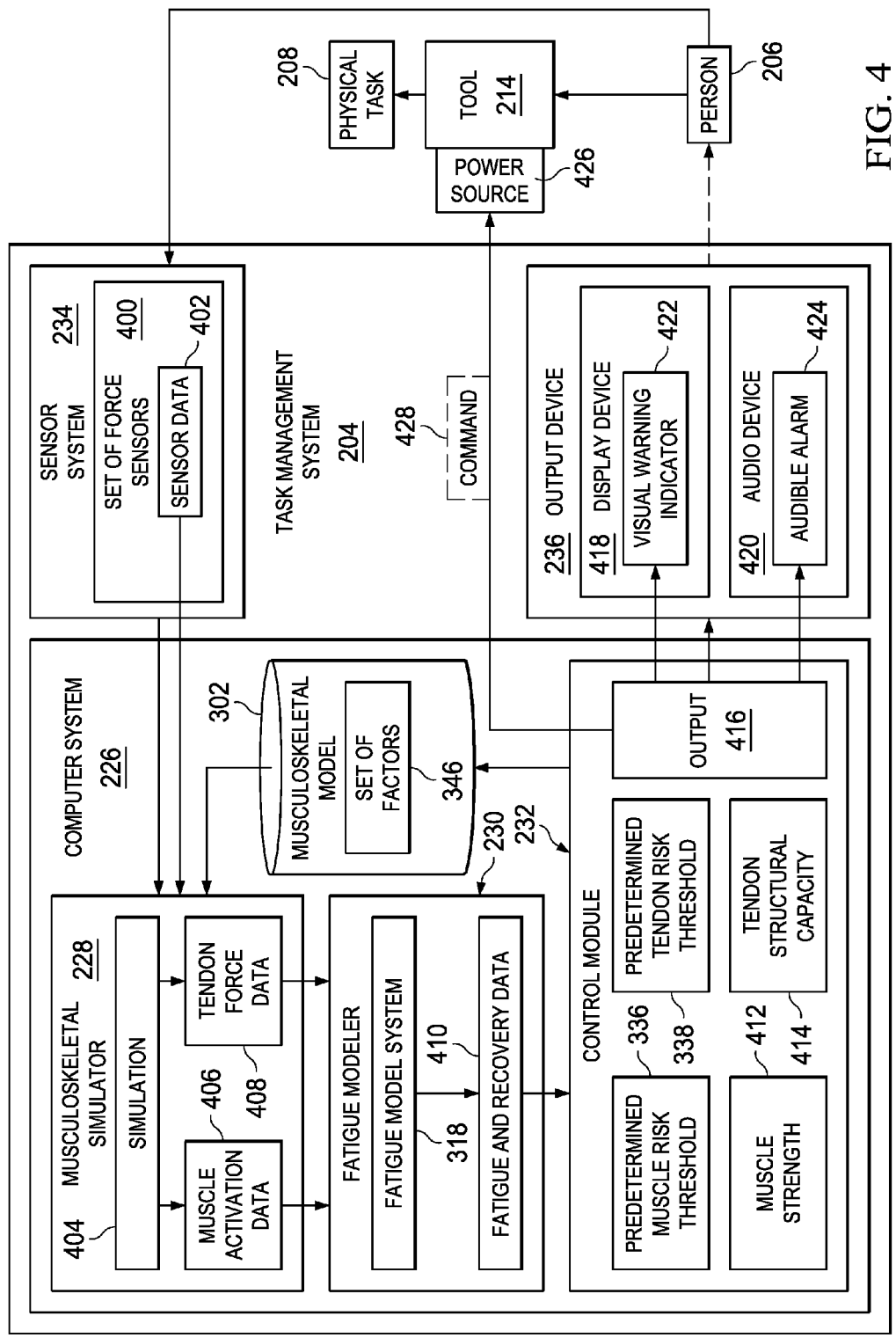
FIG. 4 is an illustration of the task management system from FIGS. 2-3 in the form of a block diagram in accordance with an illustrative embodiment.

With reference now to FIG. 4, another illustration of task management system 204 from FIGS. 2-3 is depicted in accordance with an illustrative embodiment. An example of one manner in which task management system 204 from FIGS. 2-3 may be used to monitor and quantify the musculoskeletal performance of person 206 repeatedly performing physical task 208 is described below.

Sensor system 234 may be used to monitor person 206 repeatedly performing physical task 208 using tool 214 to generate task performance data. Sensor system 234 may include at least one sensor capable of measuring motion data, force data, or both. Depending on the implementation, sensor system 234 may include at least one sensor configured to be positioned on the limb of person 206 or relative to some other body part of person 206.

Further, sensor system 234 is in communication with musculoskeletal simulator 228. Depending on the implementation, sensor system 234 may communicate with musculoskeletal simulator 228 using at least one of a wireless communications link, a wired communications link, an optical communications link, or some other type of communications link.

In one illustrative example, sensor system 234 includes set of force sensors 400 that generate sensor data 402 for each repetition of physical task 208 performed by person 206. Sensor data 402 may be task performance data. Sensor system 234 sends sensor data 402 to musculoskeletal simulator 228. Musculoskeletal simulator 228 runs simulation 404 using sensor data 402 and musculoskeletal model 302 to generate muscle activation data 406 and tendon force data 408.

In other illustrative examples, musculoskeletal simulator 228 may receive only time information about when the performance of the number of repetitions of physical task 208 begins. Musculoskeletal simulator 228 may use task description data 304 from FIG. 3 and musculoskeletal model 302 to generate muscle activation data 406 and tendon force data 408 for each repetition of physical task 208. In some cases, musculoskeletal model 302 may be tuned to the anthropometric makeup of person 206, demographic factors, or both.

Musculoskeletal simulator 228 sends muscle activation data 406 and tendon force data 408 to fatigue modeler 230 for processing. Fatigue modeler 230 processes muscle activation data 406 and tendon force data 408 using fatigue model system 318 to generate fatigue and recovery data 410. Fatigue and recovery data 410 may include, for example, without limitation, muscle fatigue data 324, muscle recovery data 326, tendon fatigue data 328, and tendon recovery data 330 described in FIG. 3.

Control module 232 receives and processes fatigue and recovery data 410 to predict muscle strength 412 and tendon structural capacity 414 of person 206 after each repetition of physical task 208. Control module 232 may determine whether at least one of predetermined muscle risk threshold 336 or predetermined tendon risk threshold 338 has been passed after any given repetition of physical task 208. If at least one of predetermined muscle risk threshold 336 or predetermined tendon risk threshold 338 has been passed after a particular repetition of physical task 208, control module 232 generates output 416 to indicate risk.

In one illustrative example, output 416 is sent to output device 236. Output device 236 may include display device 418, audio device 420, or both. For example, without limitation, output 416 may include visual warning indicator 422 that is sent to display device 418 for display on display device 418. Visual warning indicator 422 may visually warn person 206 that the risk of musculoskeletal injury has increased beyond the acceptable risk threshold. Visual warning indicator 422 thus alerts person 206 to cease performing physical task 208. In some cases, output 416 may be an instruction that is displayed on display device 418 instructing person 206 to cease performing physical task 208.

In other illustrative examples, output 416 takes the form of audible alarm 424 that is played using audio device 420. Audible alarm 424 audibly alerts person 206 that the risk of musculoskeletal injury has increased beyond the acceptable risk threshold. Audible alarm 424 thus alerts person 206 to cease performing physical task 208.

In other illustrative examples, output 416 may be used to cut the supply of power from power source 426 to tool 214. Power source 426 may be part of tool 214 or external to tool 214, depending on the implementation. As one illustrative example, output 416 takes the form of command 428 that is sent to power source 426 to halt the supply of power to tool 214. Control module 232 may follow a number of safety procedures and guidelines in determining whether to send command 428 to power source 426.

In this manner, task management system 204 may function as a real-time warning system that may be used to alert persons such as manufacturing laborers when the risk of musculoskeletal injury due to the repetitive performance of a physical task has exceeded an acceptable risk threshold. This type of real-time warning system may improve overall safety in performing manufacturing operations in various types of manufacturing environments.

The illustrations of simulation environment 200 and manufacturing environment 202 in FIG. 2 and task management system 204 in FIGS. 2-4 are not meant to imply physical or architectural limitations to the manner in which an illustrative embodiment may be implemented. Other components in addition to or in place of the ones illustrated may be used. Some components may be optional. Also, the blocks are presented to illustrate some functional components. One or more of these blocks may be combined, divided, or combined and divided into different blocks when implemented in an illustrative embodiment.

Figure 5:
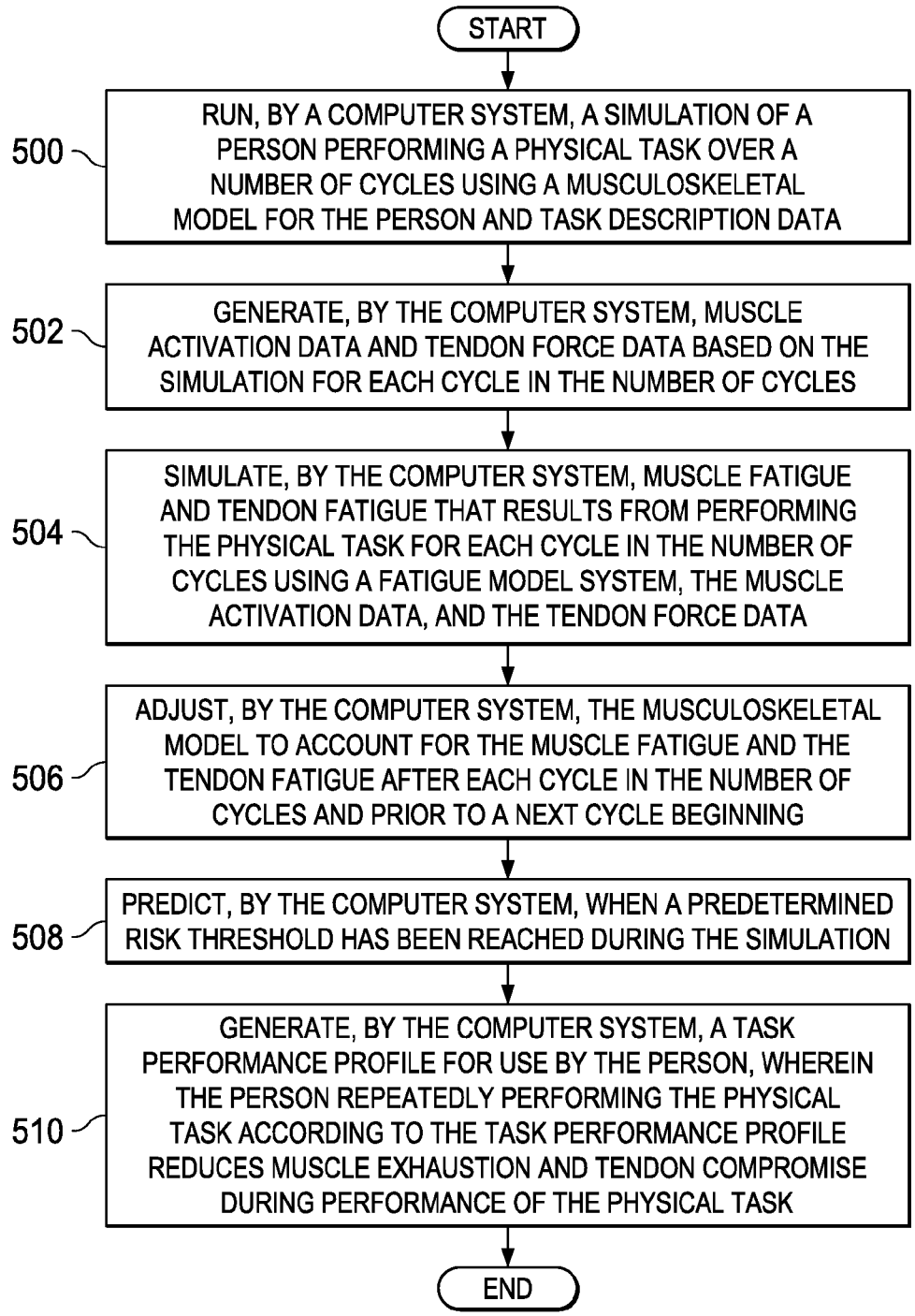
FIG. 5 is an illustration of a process for managing musculoskeletal performance in the form of a flowchart in accordance with an illustrative embodiment.

With reference now to FIG. 5, an illustration of a process for managing musculoskeletal performance is depicted in the form of a flowchart in accordance with an illustrative embodiment. The process illustrated in FIG. 5 may be performed using task management system 204 described in FIGS. 2-4. Further, this process may be performed using computer system 226 described in FIGS. 2-4.

The process may begin by running, by a computer system, a simulation of a person performing a physical task over a number of cycles using a musculoskeletal model for the person and task description data (operation 500). Next, the computer system generates muscle activation data and tendon force data based on the simulation for each cycle in the number of cycles (operation 502).

The computer system simulates muscle fatigue and tendon fatigue that results from performing the physical task for each cycle in the number of cycles using a fatigue model system, the muscle activation data, and the tendon force data (operation 504). Thereafter, the computer system adjusts the musculoskeletal model to account for the muscle fatigue and the tendon fatigue after each cycle in the number of cycles and prior to a next cycle beginning (operation 506).

The computer system predicts when a predetermined risk threshold has been reached during the simulation (operation 508). Further, the computer system generates a task performance profile for use by the person in which the person repeatedly performing the physical task according to the task performance profile reduces muscle exhaustion and tendon compromise during performance of the physical task (operation 510), with the process terminating thereafter.

Figure 6:
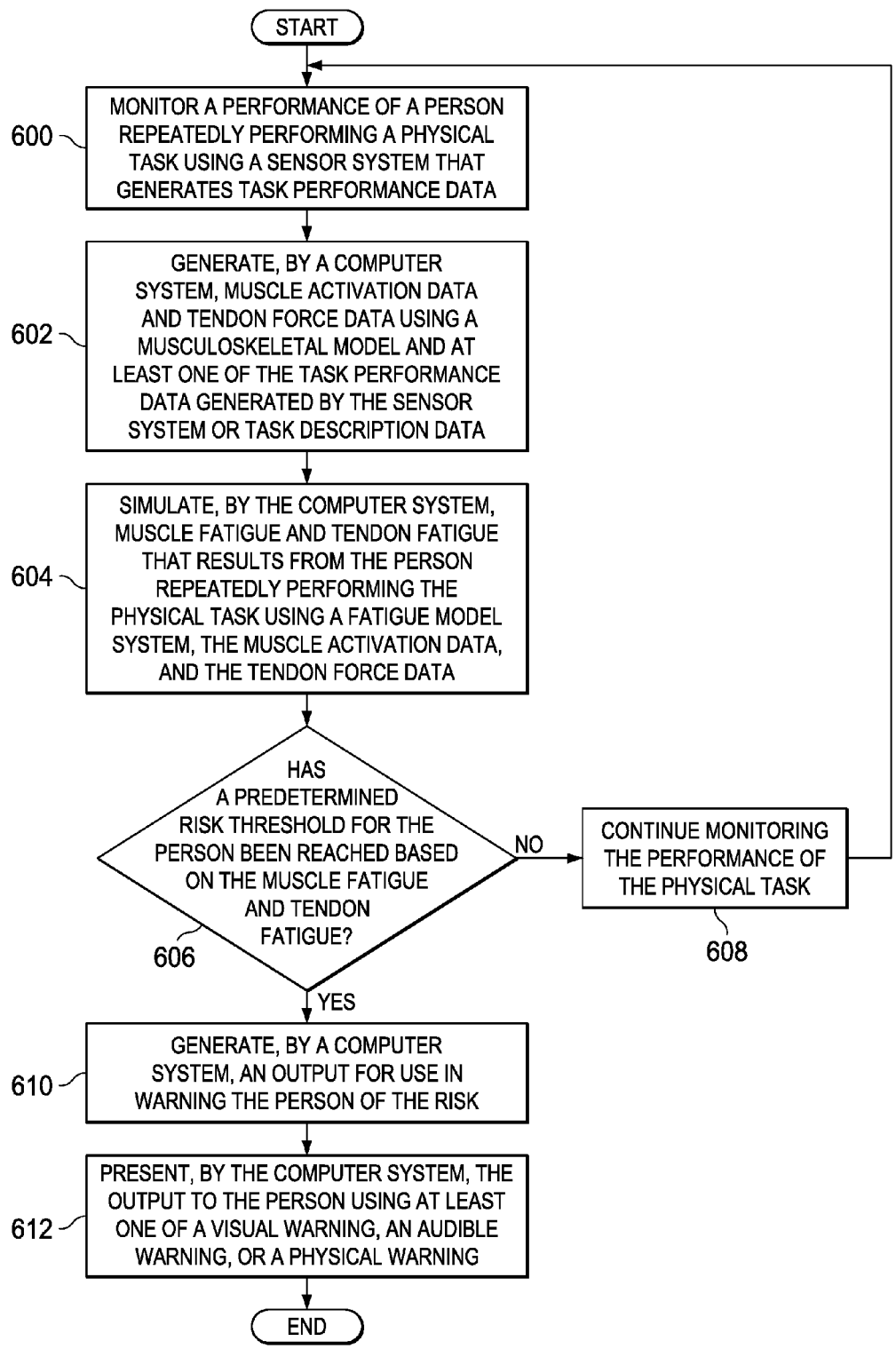
FIG. 6 is an illustration of a process for managing musculoskeletal performance during the repeated performance of a physical task in the form of a flowchart in accordance with an illustrative embodiment.

With reference now to FIG. 6, an illustration of a process for managing musculoskeletal performance during the repeated performance of a physical task is depicted in the form of a flowchart in accordance with an illustrative embodiment. The process illustrated in FIG. 6 may be performed using task management system 204 described in FIGS. 2-4.

The process may begin by monitoring a performance of a person repeatedly performing a physical task using a sensor system that generates task performance data (operation 600). The task performance data may include sensor data such as motion data, force data, or both.

Next, a computer system may generate muscle activation data and tendon force data using a musculoskeletal model and at least one of the task performance data generated by the sensor system or task description data (operation 602). The task description data may include, for example, without limitation, at least one of a time course of joint positions corresponding to the physical task, external loading conditions for the physical task, a repetition count, or some other type of information. The computer system simulates muscle fatigue and tendon fatigue that results from the person repeatedly performing the physical task using a fatigue model system, the muscle activation data, and the tendon force data (operation 604).

A determination may then be made as to whether a predetermined risk threshold for the person has been reached based on the simulated muscle fatigue and tendon fatigue (operation 606). In operation 606, this determination may be made by identifying muscle strength and tendon structural capacity for the person based on the muscle fatigue and the tendon fatigue. The muscle strength and the tendon structural capacity may be compared against predetermined risk thresholds.

If the undesired level of risk has not been reached, the process continues to monitor the performance of the physical task (operation 608), with the process returning to operation 600 described above. However, if the undesired level of risk has been reached, the computer system generates an output for use in warning the person of the risk (operation 610). Thereafter, the computer system presents the output to the person using at least one of a visual warning, an audible warning, or a physical warning (operation 612), with the process terminating thereafter.

Figure 7:
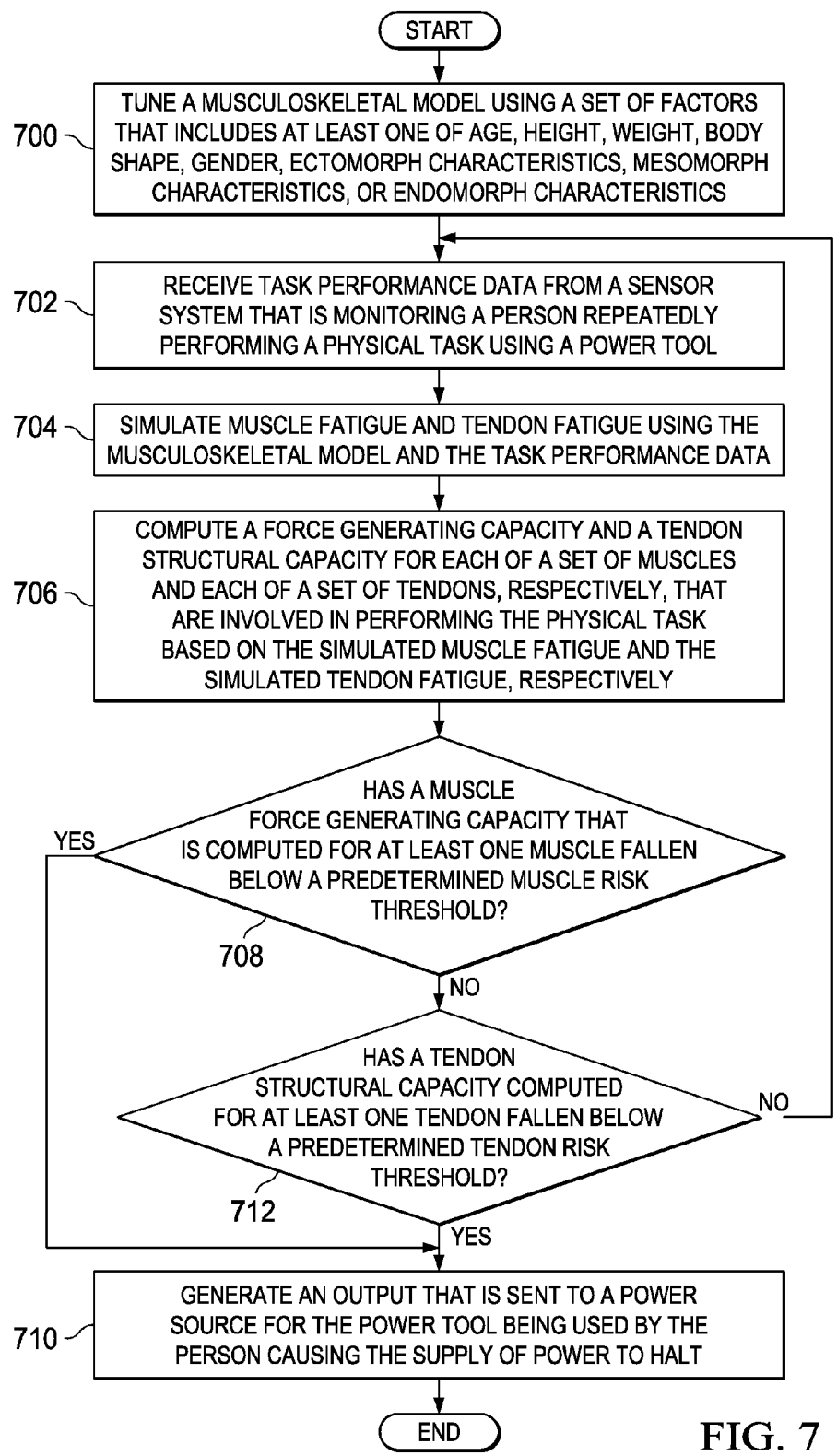
FIG. 7 is an illustration of a process for managing musculoskeletal performance during the repeated performance of a physical task in the form of a flowchart in accordance with an illustrative embodiment.

With reference now to FIG. 7, an illustration of a process for managing musculoskeletal performance during the repeated performance of a physical task is depicted in the form of a flowchart in accordance with an illustrative embodiment. The process illustrated in FIG. 7 may be performed using task management system 204 described in FIGS. 2-4.

The process begins by tuning a musculoskeletal model using a set of factors that include at least one of age, height, weight, body shape, gender, ectomorph characteristics, mesomorph characteristics, or endomorph characteristics (operation 700). Next, task performance data is received from a sensor system that is monitoring a person repeatedly performing a physical task using a power tool (operation 702).

Muscle fatigue and tendon fatigue are simulated using the musculoskeletal model and the task performance data (operation 704). In operation 704, task description data may also be used to simulate the muscle fatigue and the tendon fatigue. A force generating capacity and a tendon structural capacity are then computed for each of a set of muscles and each of a set of tendons, respectively, that are involved in performing the physical task based on the simulated muscle fatigue and the simulated tendon fatigue, respectively (operation 706).

A determination is then made as to whether a muscle force generating capacity computed for at least one muscle has fallen below a predetermined muscle risk threshold (operation 708). If the muscle force generating capacity computed for at least one muscle has fallen below the predetermined muscle risk threshold, an output is generated that is then sent to a power source for the power tool being used by the person causing the supply of power to halt (operation 710), with the process terminating thereafter.

With referenced again to operation 708, if the muscle force generating capacity computed for at least one muscle has not fallen below the predetermined muscle risk threshold, a determination is then made as to whether a tendon structural capacity computed for at least one tendon has fallen below a predetermined tendon risk threshold (operation 712). If the tendon structural capacity computed for at least one tendon has fallen below the predetermined muscle risk threshold, the process proceeds to operation 710 as described above. Otherwise, the process returns to operation 702 as described above.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 8:
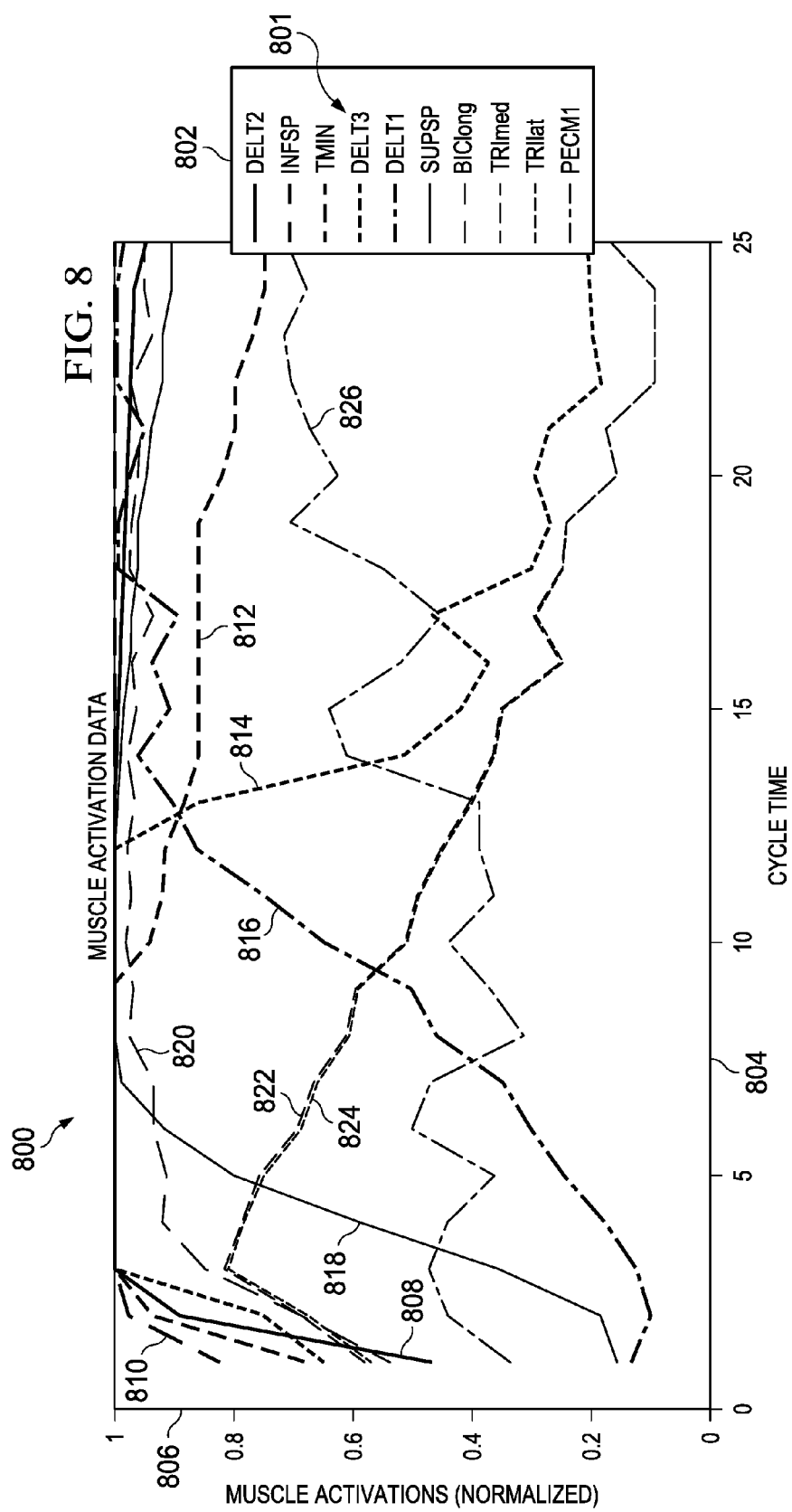
FIG. 8 is an illustration of a graph representing a muscle fatigue experiment in accordance with an illustrative embodiment.

Referring now to FIG. 8, an illustration of a graph representing a muscle fatigue experiment is depicted in accordance with an illustrative embodiment. Graph 800 includes data for muscles 801 identified in legend 802. Graph 800 has cycle time axis 804 and muscle activations axis 806. Cycle time axis 804 identifies a time over which number of cycles over which muscle activation data is collected. Muscle activations axis 806 identifies the average muscle activation for each cycle.

In this illustrative example, muscles 801 include deltoid muscle (DELT2) 808, infraspinatus muscle (INFSP) 810, *teres* minor muscle (TMIN) 812, deltoid muscle (DELT3) 814, deltoid muscle (DELT1) 816, supraspinatus muscle (SUPSP) 818, bicep muscle (BIClong) 820, medial triceps muscle (TRImed) 822, lateral triceps muscle (TRIlat) 824, and pectoralis muscle (PECM1) 826. The simulation experiment was conducted for a physical task that includes moving a three-pound object, such as a tool, in a wiping motion along a surface using about three pounds of normal force with the right hand at face level. This movement is repeated for a selected number of cycles. The wiping motion has a cycle duration of about 1 second. This motion is simulated for a period of about 25 minutes. Thus, the simulation runs for about 1500 cycles.

Muscles 801 may be the 10 most involved muscles of the right arm and chest involved in performing this physical task. Graph 800 illustrates the change in maximum isometric force in muscles 801 based on the maximum muscle activation of each muscle during the experiment. As depicted in graph 800, initially, when less fatigued, deltoid muscle 808, deltoid muscle 814, *teres* minor muscle 812, and infraspinatus muscle 810 are fully involved in performing the wiping motion. However, these muscles quickly fatigue and saturate. While medial triceps muscle 822 and lateral triceps muscle 824 help, these muscles also quickly fatigue and their contributions diminish.

One change shown in graph 800 is the muscle activation level for deltoid muscle 814, which drops precipitously from the $1^{st}$ minute of the experiment to a muscle activation level below about 0.4 (or 40 percent of normal muscle activation level) by the 16$^{th}$ minute. Deltoid muscle 814 is a key muscle for the wiping motion. To compensate for the loss of key muscle activation, activation of supraspinatus muscle 818 of the rotator cuff rises from about 0.2 to about 1.0 by the 7$^{th}$ minute. Further, deltoid muscle 816, which was not initially involved in the movement, rises to more than about 0.9 by the 14$^{th}$ minute. The depicted rise in muscle activation levels of these compensatory muscles may cause muscle imbalances and thereby raise the risk of injury beyond an acceptable risk threshold.

Accordingly, from the depicted normal muscle activation levels shown in FIG. 8 corresponding to the repetitive wiping motion of a three pound object or tool, a fatigue modeler module, such as fatigue modeler 230 from FIGS. 2-4, may simulate muscle fatigue. The simulated muscle fatigue may be used to determine when muscle strength declines to a point at which a predetermined muscle risk threshold is reached or passed. As one illustrative example, the predetermined muscle risk threshold may be a muscle force generating capacity for a muscle that is between about 40 percent and about 80 percent.

Similarly, the fatigue modeler module may simulate tendon fatigue. The simulated tendon fatigue may be used to determine when tendon structural capacity declines to a point at which a predetermined tendon risk threshold is reached or passed. In one illustrative example, the predetermined tendon risk threshold may be a tendon structural capacity for a tendon that is between about 40 percent and about 80 percent.

Based on the information collected above, a sensor system, such as sensor system 234 in FIG. 2 and FIG. 4, may be used to monitor a person repeatedly performing the physical task using the three pound object or tool by moving the object or tool with the wiping motion described above. A control module, such as control module 232 in FIGS. 2-4, may generate an output when, with respect to the number of repetitions of the physical task or movements sensed by the sensor system, the predetermined muscle risk threshold or predetermined tendon risk threshold has been reached or passed. For example, without limitation, the control module may generate a visual warning indicator for display on a display device, an audible alarm for playing on an audio device, or a command to be sent to interrupt the supply of power from a power source to the object or tool used by the person. In this manner, the output may be used to at least one of visually, audibly, or physically alert the person of the undesirable level of risk for injury.

Figure 9:
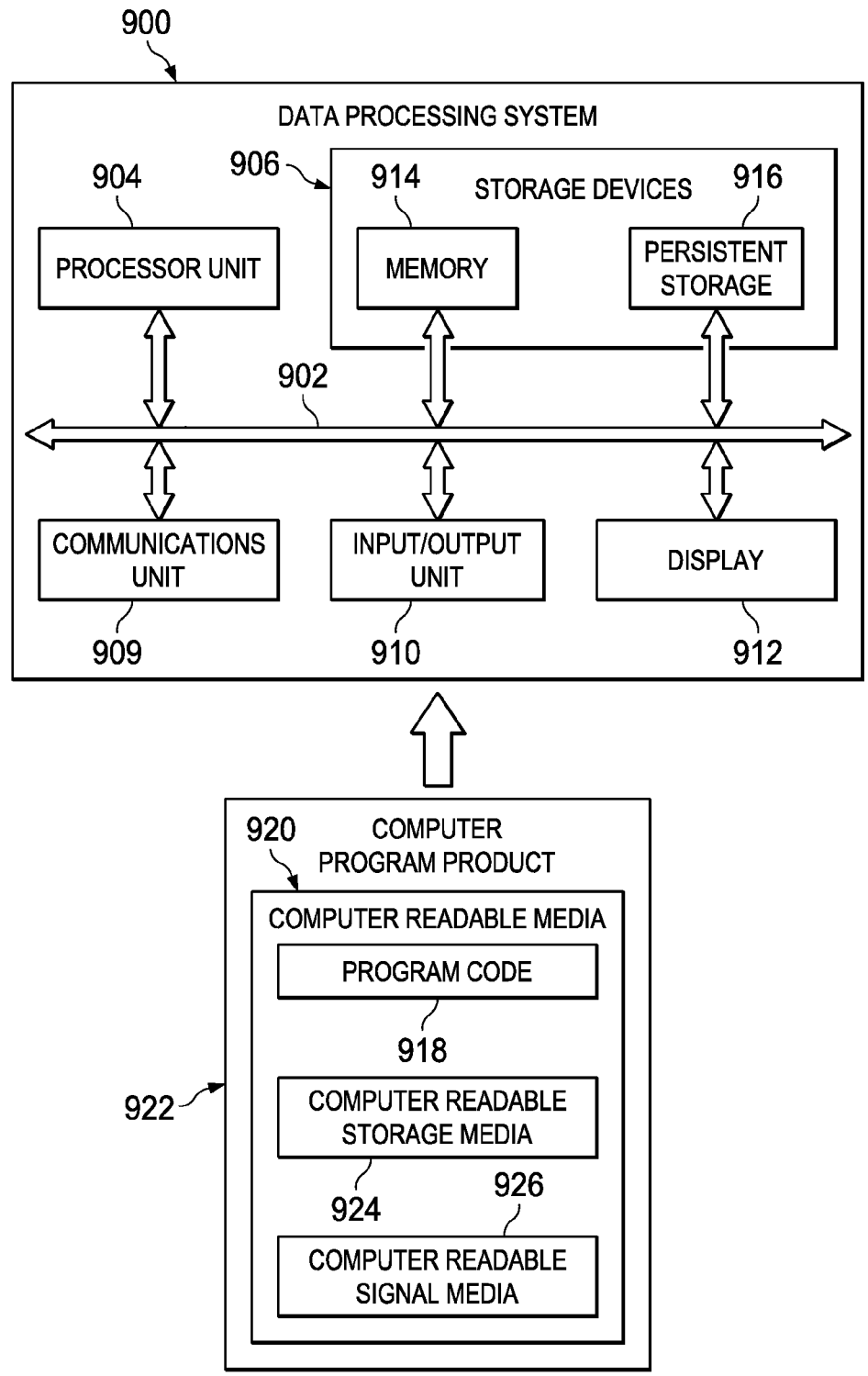
FIG. 9 is an illustration of a data processing system in the form of a block diagram in accordance with an illustrative embodiment.

Turning now to FIG. 9, an illustration of a data processing system in the form of a block diagram is depicted in accordance with an illustrative embodiment. Data processing system 900 may be used to implement at least one of computer system 226, musculoskeletal simulator 228, fatigue modeler 230, or control module 232 in FIGS. 2-4. As depicted, data processing system 900 includes communications framework 902, which provides communications between processor unit 904, storage devices 906, communications unit 908, input/output unit 910, and display 912. In some cases, communications framework 902 may be implemented as a bus system.

Processor unit 904 is configured to execute instructions for software to perform a number of operations. Processor unit 904 may comprise a number of processors, a multiprocessor core, and/or some other type of processor, depending on the implementation. In some cases, processor unit 904 may take the form of a hardware unit, such as a circuit system, an application specific integrated circuit (ASIC), a programmable logic device, or some other suitable type of hardware unit.

Instructions for the operating system, applications, and/or programs run by processor unit 904 may be located in storage devices 906. Storage devices 906 may be in communication with processor unit 904 through communications framework 902. As used herein, a storage device, also referred to as a computer readable storage device, is any piece of hardware capable of storing information on a temporary and/or permanent basis. This information may include, but is not limited to, data, program code, and/or other information.

Memory 914 and persistent storage 916 are examples of storage devices 906. Memory 914 may take the form of, for example, a random access memory or some type of volatile or non-volatile storage device. Persistent storage 916 may comprise any number of components or devices. For example, persistent storage 916 may comprise a hard drive, a flash memory, a rewritable optical disk, a rewritable magnetic tape, or some combination of the above. The media used by persistent storage 916 may or may not be removable.

Communications unit 908 allows data processing system 900 to communicate with other data processing systems and/or devices. Communications unit 908 may provide communications using physical and/or wireless communications links.

Input/output unit 910 allows input to be received from and output to be sent to other devices connected to data processing system 900. For example, input/output unit 910 may allow user input to be received through a keyboard, a mouse, and/or some other type of input device. As another example, input/output unit 910 may allow output to be sent to a printer connected to data processing system 900.

Display 912 is configured to display information to a user. Display 912 may comprise, for example, without limitation, a monitor, a touch screen, a laser display, a holographic display, a virtual display device, and/or some other type of display device.

In this illustrative example, the processes of the different illustrative embodiments may be performed by processor unit 904 using computer-implemented instructions. These instructions may be referred to as program code, computer usable program code, or computer readable program code and may be read and executed by one or more processors in processor unit 904.

In these examples, program code 918 is located in a functional form on computer readable media 920, which is selectively removable, and may be loaded onto or transferred to data processing system 900 for execution by processor unit 904. Program code 918 and computer readable media 920 together form computer program product 922. In this illustrative example, computer readable media 920 may be computer readable storage media 924 or computer readable signal media 926.

Computer readable storage media 924 is a physical or tangible storage device used to store program code 918 rather than a medium that propagates or transmits program code 918. Computer readable storage media 924 may be, for example, without limitation, an optical or magnetic disk or a persistent storage device that is connected to data processing system 900.

Alternatively, program code 918 may be transferred to data processing system 900 using computer readable signal media 926. Computer readable signal media 926 may be, for example, a propagated data signal containing program code 918. This data signal may be an electromagnetic signal, an optical signal, and/or some other type of signal that can be transmitted over physical and/or wireless communications links.

The illustration of data processing system 900 in FIG. 9 is not meant to provide architectural limitations to the manner in which the illustrative embodiments may be implemented. The different illustrative embodiments may be implemented in a data processing system that includes components in addition to or in place of those illustrated for data processing system 900. Further, components shown in FIG. 9 may be varied from the illustrative examples shown.

Figure 10:
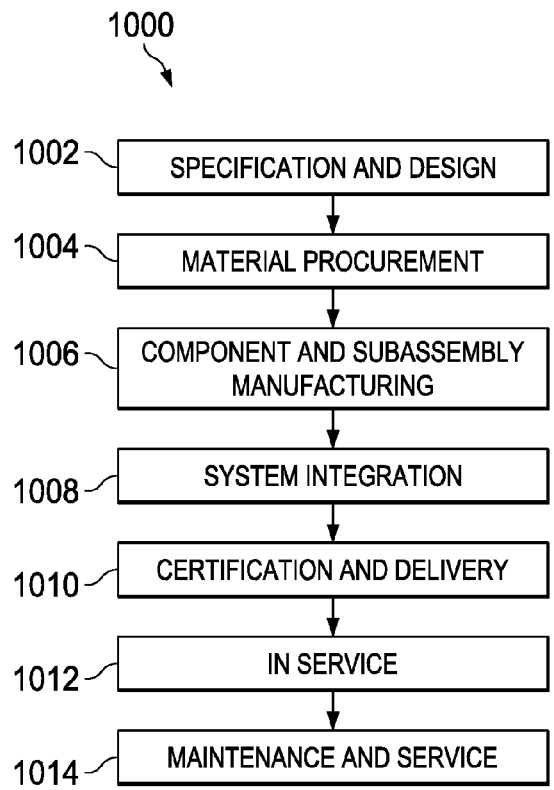
FIG. 10 is an illustration of an aircraft manufacturing and service method in the form of a block diagram in accordance with an illustrative embodiment.
Figure 11:
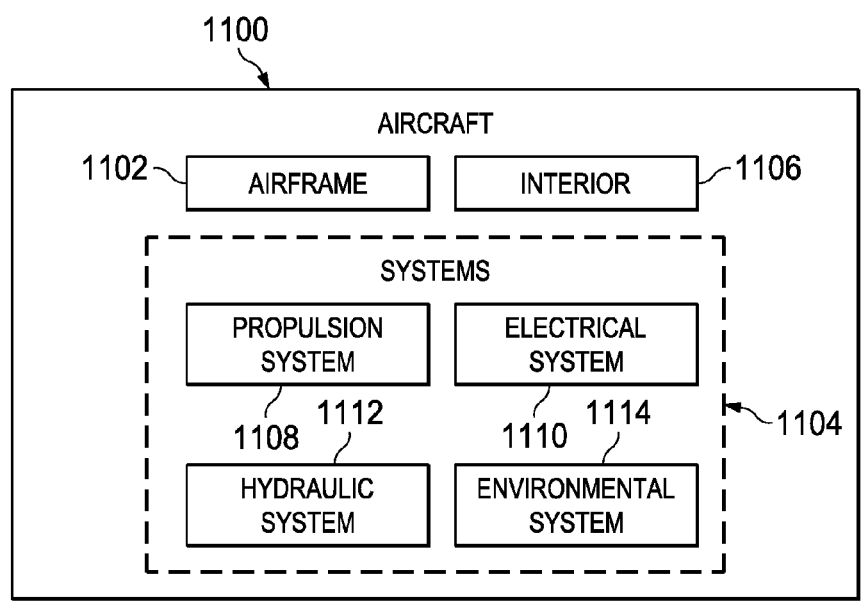
FIG. 11 is an illustration of an aircraft in the form of a block diagram in accordance with an illustrative embodiment.

Illustrative embodiments of the disclosure may be described in the context of aircraft manufacturing and service method 1000 as shown in FIG. 10 and aircraft 1100 as shown in FIG. 11. Turning first to FIG. 10, an illustration of an aircraft manufacturing and service method is depicted in accordance with an illustrative embodiment. During pre-production, aircraft manufacturing and service method 1000 may include specification and design 1002 of aircraft 1100 in FIG. 11 and material procurement 1004.

During production, component and subassembly manufacturing 1006 and system integration 1008 of aircraft 1100 in FIG. 11 takes place. Thereafter, aircraft 1100 in FIG. 11 may go through certification and delivery 1010 in order to be placed in service 1012. While in service 1012 by a customer, aircraft 1100 in FIG. 11 is scheduled for routine maintenance and service 1014, which may include modification, reconfiguration, refurbishment, and other maintenance or services.

Each of the processes of aircraft manufacturing and service method 1000 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 11, an illustration of an aircraft is depicted in which an illustrative embodiment may be implemented. In this example, aircraft 1100 is produced by aircraft manufacturing and service method 1000 in FIG. 10 and may include airframe 1102 with systems 1104 and interior 1106. Examples of systems 1104 include one or more of propulsion system 1108, electrical system 1110, hydraulic system 1112, and environmental system 1114. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1000 in FIG. 10. In particular, task management system 204 from FIGS. 2-4 may be used to monitor and quantify musculoskeletal performance for repetitive physical tasks that are performed during any one of the stages of aircraft manufacturing and service method 1000. For example, without limitation, task management system 204 from FIGS. 2-4 may be used to monitor a person repeatedly performing a task during at least one of component and subassembly manufacturing 1006, system integration 1008, routine maintenance and service 1014, or some other stage of aircraft manufacturing and service method 1000. Task management system 204 may alert the person visually, audibly, physically, or in some other manner when a risk of musculoskeletal injury has increased beyond an acceptable risk threshold.

In one illustrative example, components or subassemblies produced in component and subassembly manufacturing 1006 in FIG. 10 may be fabricated or manufactured in a manner similar to components or subassemblies produced while aircraft 1100 is in service 1012 in FIG. 10. As yet another example, one or more apparatus embodiments, method embodiments, or a combination thereof may be utilized during production stages, such as component and subassembly manufacturing 1006 and system integration 1008 in FIG. 10. One or more apparatus embodiments, method embodiments, or a combination thereof may be utilized while aircraft 1100 is in service 1012 and/or during maintenance and service 1014 in FIG. 10. The use of a number of the different illustrative embodiments may substantially expedite the assembly of and/or reduce the cost of aircraft 1100.

Thus, the illustrative embodiments provide a method and apparatus for monitoring a person performing repetition musculoskeletal movements corresponding to a manufacturing operation and estimating muscle fatigue and tendon fatigue for use in alerting the person as to a predetermined risk threshold has been reached with respect to a level of risk of musculoskeletal injury to the person. The person may be alerted visually, audibly, physically, or in some other manner.

The person may be actively monitored using a sensor system or passively monitored. Thus, the muscle fatigue and tendon fatigue may be estimated based on simulations, real-time motion and force data generated using the sensor system, or both. The method and apparatus allow quantification of the muscle fatigue and tendon fatigue after each iteration of performing a particular physical task such that muscle strength and tendon structural capacity remaining after the iteration may be identified.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for monitoring musculoskeletal performance, the method comprising:
    monitoring a performance of a person repeatedly performing a physical task using a sensor system to generate task performance data;
    running, by a computer system, a simulation of the person performing the physical task over a number of cycles using a musculoskeletal model for the person and at least one of the task performance data and task description data;
    generating, by the computer system, muscle activation data and tendon force data based on the simulation for each cycle in the number of cycles;
    simulating, by the computer system, muscle fatigue and tendon fatigue that results from performing the physical task for the each cycle in the number of cycles using a fatigue model system, the muscle activation data, and the tendon force data;

adjusting, by the computer system, the musculoskeletal model to account for the muscle fatigue and the tendon fatigue after the each cycle in the number of cycles and prior to a next cycle beginning; and predicting, by the computer system, when a predetermined risk threshold for the person is reached based on the simulation.

2. The method of claim 1, wherein generating, by the computer system, the muscle activation data and the tendon force data comprises:

generating the muscle activation data and the tendon force data using the musculoskeletal model and at least one of the task performance data generated by the sensor system or the task description data.

3. The method of claim 1 further comprising:

generating, by the computer system, an alert that indicates an undesired level of risk for the person when the predetermined risk threshold has been reached.

4. The method of claim 1 further comprising:

generating, by the computer system, a task performance profile for use by the person, wherein the person repeatedly performing the physical task according to the task performance profile reduces muscle exhaustion and tendon compromise during performance of the physical task.

5. The method of claim 1 further comprising:

generating, by the computer system, an output indicating that the predetermined risk threshold for the person has been reached; and presenting, by the computer system, the output to the person using an output device to alert the person that the predetermined risk threshold has been reached.

6. The method of claim 5, wherein presenting, by the computer system, the output to the person comprises:

displaying a visual warning indicator on a display device to visually warn the person that the predetermined risk threshold has been passed.

7. The method of claim 5, wherein presenting, by the computer system, the output to the person comprises:

generating an audible alarm using an audio device to audibly warn the person that the predetermined risk threshold has been passed.

8. The method of claim 5, wherein presenting, by the computer system, the output to the person comprises:

displaying an instruction on a display device for instructing the person to cease performing the physical task due to the predetermined risk threshold being passed.

9. The method of claim 5, wherein presenting, by the computer system, the output to the person comprises:

sending a command to a tool, which is being used by the person to perform the physical task, that halts operation of the tool, thereby preventing the person from being able to continue performing the physical task.

10. The method of claim 1 further comprising:

generating an output that is sent to a power source that supplies power to a tool being used by the person to perform the physical task when the predetermined risk threshold has been passed.

11. The method of claim 1, wherein generating, by the computer system, the muscle activation data and the tendon force data comprises:

computing a muscle activation metric for a set of muscles needed to perform the physical task during a cycle of the number of cycles using the musculoskeletal model and the task description data; and computing a number of forces exerted on a set of tendons over the cycle using the musculoskeletal model and the task description data.

12. The method of claim 1 further comprising:

receiving, by the computer system, the task description data, wherein the task description data identifies at least one of a time course of joint positions corresponding to performance of the physical task, an external loading experienced during performance of the physical task, and a number of repetitions for the physical task.

13. The method of claim 1, wherein predicting, by the computer system, when the predetermined risk threshold has been passed during the simulation comprises:

determining when a muscle force generating capacity that is computed for at least one muscle of the person performing the physical task falls below a predetermined muscle risk threshold; and determining when a tendon structural capacity computed for at least one tendon of the person performing the physical task falls below a predetermined tendon risk threshold.

14. The method of claim 1 further comprising:

tuning the musculoskeletal model using a set of factors that includes at least one of age, height, weight, body shape, gender, ectomorph characteristics, endomorph characteristics, or mesomorph characteristics.

15. An apparatus comprising:

a sensor system that monitors a person repeatedly performing a physical task to generate task performance data;

a musculoskeletal simulator module in communication with the sensor system and implemented in a computer system, wherein the musculoskeletal simulator module runs a simulation of the person performing the physical task over a number of cycles using a musculoskeletal model for the person and at least one of the task performance data or task description data and generates muscle activation data and tendon force data based on the simulation for each cycle in the number of cycles;

a fatigue modeler module implemented in the computer system that simulates muscle fatigue and tendon fatigue that results from performing the physical task for the each cycle in the number of cycles using a fatigue model system, the muscle activation data, and the tendon force data, wherein the musculoskeletal model is adjusted to account for the muscle fatigue and the tendon fatigue after the each cycle in the number of cycles and prior to a next cycle beginning; and a control module implemented in the computer system that predicts when a predetermined risk threshold for the person is reached based on the simulation.

16. The apparatus of claim 15, wherein the control module generates a task performance profile for use by the person such that the person repeatedly performing the physical task according to the task performance profile reduces muscle exhaustion and tendon compromise during performance of the physical task.

17. The apparatus of claim 16, wherein the sensor system comprises at least one sensor that is configured to be positioned on a limb of the person to measure motion and force data for the person repeatedly performing the physical task.

18. The apparatus of claim 15 further comprising:
an output device in communication with the control module that presents an output indicating that an undesired level of risk for the person performing the physical task has been reached to the person.

19. The apparatus of claim 18, wherein the output comprises at least one of a visual warning indicator for visually warning the person that the predetermined risk threshold has been passed, an audible alarm for audibly warning the person that the predetermined risk threshold has been passed, or an instruction for instructing the person to cease performing the physical task due to the predetermined risk threshold being passed.

20. The apparatus of claim 15, wherein the predetermined risk threshold is passed when at least one of a predetermined muscle risk threshold or a predetermined tendon risk threshold is passed and wherein the predetermined muscle risk threshold is a muscle force generating capacity for a muscle of the person performing the physical task that is between about 40 percent and about 80 percent and wherein the predetermined tendon risk threshold is a tendon structural capacity for a tendon of the person performing the physical task that is between about 40 percent and about 80 percent.

21. The apparatus of claim 19, wherein the sensor system monitors the person repeatedly performing the physical task of a manufacturing operation using a tool, and wherein the control module is configured to generate the output that is sent to a power source that supplies power to the tool being used by the person to interrupt power to the tool when the predetermined risk threshold has been passed.

* * * * *